United States Patent [19]

Sarantakis

[11] 4,196,122
[45] Apr. 1, 1980

[54] ANALGESIC POLYPEPTIDE

[75] Inventor: Dimitrios Sarantakis, West Chester, Pa.

[73] Assignee: American Home Products Corporation, New York, N.Y.

[21] Appl. No.: 812,039

[22] Filed: Jul. 1, 1977

[51] Int. Cl.$^2$ .................... C07C 103/52; A61K 37/00
[52] U.S. Cl. .............................. 260/112.5 R; 424/177
[58] Field of Search ................. 260/112.5 R; 424/177

[56] References Cited
PUBLICATIONS

Coy, et al., Biochem. and Biophys. Res. Commun. 73, 1976 pp. 632–637.
Walker, et al., Science 196, 1977, pp. 85–87.
Plotnikoff, et al., Life Science 19, 1976, pp. 1283–1287.
Terenius, et al., Biochem. and Biophys. Res. Commun. 71, 1976, pp. 175–179.
Kastin, et al., Pharm. Biochem. & Behavior 5, pp. 691–695, 1976.
Pert, et al., Opiates and Endogenous Opioids Peptides 1976, pp. 79–86.
Belluzzi, Nature 262, pp. 738–739, 1976.
Pert, et al., Science 194, pp. 330–332, 1976.
Beddell, et al., Proc. R. Soc. 198, 249–265, 1977.

*Primary Examiner*—Delbert R. Phillips
*Attorney, Agent, or Firm*—Richard K. Jackson

[57] ABSTRACT

The polypeptides of the formula:

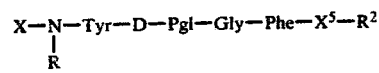

in which
X is hydrogen, Arg, Lys or Orn;
$X^5$ is a D-α-amino acid;
R is hydrogen, methyl, allyl or cyclopropylmethyl;
and
$R^2$ is —OH, —NH$_2$ or —NHC$_n$H$_{2n+1}$ where n is 1, 2, 3 or 4 or a pharmaceutically acceptable salt thereof, exert an analgesic effect in warm-blooded animals when peripherally administered.

8 Claims, No Drawings

ANALGESIC POLYPEPTIDE

BACKGROUND OF THE INVENTION

Enkephalin, a natural opiate receptor agonist in the brain, has been identified [see Hughes et al., Nature 256, 577(1975)] as a mixture of two pentapeptides: H-Tyr-Gly-Gly-Phe-Met-OH (methionine-enkephalin) and H-Tyr-Gly-Gly-Phe-Leu-OH (leucine-enkephalin). Both peptides mimic the ability of morphine to block electrically evoked contractions of mouse vas deferens and guinea pig ileum, and both inhibit the stereospecific receptor binding of the opiate antagonist 3H-naloxone in brain homogenates.

It has been proposed that enkephalin receptors may be sites at which morphine-like drugs exert their analgesic activities, and that enkephalin may be the modulator or transmitter in brain systems for pain suppression or analgesia. It has been reported that methionine-enkephalin and leucine-enkephalin, when administered by injection in the brain ventricle in rats, induce a profound analgesia that is fully reversible by naloxone. [See Beluzzi et al., Nature, 260, 625(1976)]. The enkephalins are inactive when administered peripherally, however, and it is believed that the enkephalins are rapidly destroyed by blood enzymes and/or are poorly trapported across the blood-brain barrier.

The amino acid sequence of methionine-enkephalin is identical to that of the N-terminal portion of the C-fragment ($\beta$-endorphin or $\beta$-LPH[61-91]) of the peptide $\beta$-lipotropin, which is found in large concentrations in the pituitary and in much lower concentrations in the brain. Other naturally-occuring fragments of $\beta$-lipotropin are known, for example: $\alpha$-endorphin ($\beta$-LPH[61-76]) and $\gamma$-endorphin ($\beta$-LPH[61-77]). Both $\beta$-lipotropin and the endorphins show morphine-like properties in various test systems, and it has been suggested that methionine-enkephalin is a breakdown product of the large opiate-like peptides. Enkephalin, its relationship to $\beta$-lipotropin and the endorphins, and the pharmacological properties thereof, are reviewed in an article by Iverson et al., Nature, 262, 738(1976). Recent developments are also described in detail in the "Proceedings of the International Narcotics Research Club Meeting, Abderdeen, U.K., July 19–22, 1976," published in *OPIATES AND ENDOGENOUS OPIOID PEPTIDES*, North Holland Publishing Company, Amsterdam, 1976.

Various structural variations of methionine-enkephalin and leucine-enkephalin are described in the literature. For example, the pentapeptide H-Tyr-Gly-Gly-Phe-Thr-OH, wherein the fifth amino acid residue (methionine or leucine) is replaced by threonine, is described by Chang et al., Life Sciences, 18, 1473 (1976). Similarly, a long acting synthetic pentapeptide, Tyr-D-Ala-Gly-Phe-Met-amide is described in Pert et al., Science, 194, 330 (1976); which compound, like the natural enkephalins, is inactive when administered peripherally. Baxter et al., British Journal of Pharmacology, Mar. 2, 1977, pages 455P–456P and 523P report activity in the compound Tyr-D-Ala-Gly-Phe-D-Leu when administered intracerebroventricularly.

DESCRIPTION OF THE INVENTION

In accordance with this invention, there is provided a group of polypeptides of the formula:

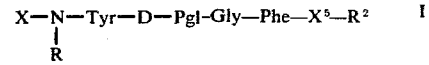

in which
 X is hydrogen, Arg, Lys or Orn;
 $X^5$ is a D-$\alpha$-amino acid;
 R is hydrogen, methyl, allyl or cyclopropylmethyl; and
 $R^2$ is —OH, —NH$_2$ or —NHC$_n$H$_{2n+1}$ where n is 1,2,3 or 4
or a pharmaceutically acceptable salt thereof.

All chiral amino acid residues in formula I and throughout this disclosure are in the natural or L-configuration unless otherwise indicated. The abbreviation D-Pgl stands for D-C-phenylglycine which has no natural L-conformer.

The preferred compounds are those of formula II:

where $X^5$ is D-Lys, D-Arg, D-Met or D-Leu, and R is hydrogen, methyl, allyl or cyclopropylmethyl, or a pharmaceutically acceptable acid addition salt thereof.

The pharmaceutically acceptable salts of the polypeptides of this invention are acid addition salts of the free base in which the acid may be either organic or inorganic, as for example, hydrochloric, phosphoric, maleic, acetic, citric, succinic, malic, and similar acids. Likewise, salts of the free peptidic acid are embraced by the expression "pharmaceutically acceptable salts", and include the sodium, potassium, ammonium, and lower alkylamine salts. The salts are prepared and isolated by conventional methods.

The analgesic polypeptides of this invention are prepared by typical solid phase procedures employing either a benzhydrylamine polystyrene based resin for the production of the C-terminal amides or a chloromethylated or hydroxy methylated divinyl benzene crosslinked polystyrene resin for production of the C-terminal carboxylic acid or lower alkylamides. The polypeptide is removed from the resin support with HF and purified by gel filtration.

The N-substituted tyrosine reactants employed in the production of the compounds disclosed herein are readily prepared by reaction of methylchloride, allylchloride or cyclopropylmethyl chloride with a Boc-tyrosyl ester in the presence of silver oxide. The product is then saponified and hydrolyzed to obtain the desired reactant.

The analgesic activity of the polypeptides of this invention was demonstrated by the method of D'Amour and Smith, J. Pharmacol. Exp. Ther., 72, 74 (1941). The representative polypeptide of this invention, Tyr-D-Pgl-Gly-Phe-D-Lys-NH$_2$, gave the following results in the reference standard rat-tail flick test:

| Dose milligram/kilogram intravenous | No. showing analgesia/No. tested |
|---|---|
| 0.5 | 0/6 |
| 1.0 | 3/6 |
| 2.5 | 6/6 |
| 5.0 | 6/6 |
| subcutaneous | |
| 5 | 1/6 |

| Dose milligram/kilogram intravenous | No. showing analgesia/No. tested |
|---|---|
| 10 | 1/6 |

The test results demonstrate that the compounds of this invention induce analgesia upon administration of a single intravenous injection of about 1.0 milligrams per kilogram or more. For practical purposes, it is contemplated, based upon the preceding test results, that a dose of from about 1 to about 10 milligrams per kilogram in single or plural doses is the appropriate dosage to achieve that degree of analgesia desired for various applications. The exact dose to be employed will, of course, vary somewhat with the specific compound employed, the patient and the degree of analgesia desired. The determination of a precise dose for production of a desired effect is readily determined empirically by the physician.

The following examples illustrate the preparation of the polypeptides of the invention.

EXAMPLE I tert-Butyloxycarbonyl-O-benzyl-L-tyrosyl-D-C-phenylglycyl-glycyl-L-phenylalanyl-ε-2-chlorobenzyloxycarbonyl-D-lysyl-benzhydrylamine polystyrene resin Seven grams of benzhydrylamine resin (Bachem, Inc.) which had been neutralized with 12 percent triethylamine in DMF was treated in a solid phase reactor with Boc-D-Lys(Clz)-OH and 1M DIC in DMF to obtain the Boc-D-Lys(Clz)-substituted resin. The resin was then washed in the reaction in accordance with steps 11 and 12 of the following schedule A. The ninhydrin test was negative. Boc-Phe-OH, Boc-Gly-OH, Boc-D-Pgl-OH and Boc-Tyr(Bzl)-OH were then incorporated individually into the peptido resin in accordance with the procedure set forth in schedule A to obtain the title compound.

Schedule A

1. Wash with $CH_2Cl_2 \times 3$.
2. Treat with TFA-$CH_2Cl_2$-EDT (1:1:5%, v/v) for 5 min.
3. Treat as in 2 for 25 min.
4. Wash with $CH_2Cl_2 \times 3$.
5. Wash with DMF.
6. Treat with 12% TEA in DMF twice for 3 min.
7. Wash with DMF.
8. Wash with $CH_2Cl_2 \times 3$.
9. Treat with 4 equivalents of the corresponding amino acid derivative in $CH_2Cl_2$DMF and stir for 5 min.
10. Add in two portions 5 equivalents of DIC dissolved in $CH_2Cl_2$ and over a period of 30 min. Reaction time 6 hours.
11. Wash with DMF $\times 3$.
12. Wash with $CH_2Cl_2 \times 3$.
13. Test ninhydrin reaction according to Kaiser et al., *Annal. Biochem.* 34, 595(1970). In case of incomplete reaction repeat lines 9 to 13 as above.

EXAMPLE 2

L-Tyrosyl-D-C-phenylglycyl-glycyl-L-phenylalanyl-D-lysyl amide

The peptidoresin of the previous example (8 g.) was mixed with anisole (15 ml.) and treated with anhydrous liquid HF (150 ml.) for 45 minutes at 18° C. The excess HF was removed as fast as possible (ca. 60 minutes) under vacuo and the residue was taken in 10% aqueous acetic acid and filtered. The filtrate was treated with BioRad AG 3 (Acetate form), filtered, and the filtrate was lyophilized to afford 174 mg. of crude material. This material was applied onto a column of Sephandex G-15 (1.5 $\times$ 80 cm) and eluted with 10% aqueous acetic acid. The material which emerged in tubes 24 to 39 was pooled and lyophilized to yield 114 mg. of the title compound as the diacetate salt. TLC Avicel precoated glass plates, Rf (BWA, 4:1:1, v/v) 0.48, Rf (tert-AmOH-W-Py, 7:6:7, v/v) 0.65. Aminoacid analysis: Gly (1) 1, Tyr (1) 0.90, Phe (1) 1, Lys (1) 1.04, $NH_3$ (1) 1.61, Pgl (1) N.D.

EXAMPLE 3

L-Tyrosyl-D-C-phenylglycyl-glycyl-L-phenylalanyl-D-methionyl amide

By initially introducing Boc-D-Met-OH into the benzhydrylamine polystyrene based resin in accordance with the procedure of example 1, followed by the sequential coupling of Boc-Phe-OH, Boc-Gly-OH, Boc-Pgl-OH and Boc-Tyr(Bzl)-OH by the technique of schedule A, yields the peptido resin from which the title compound is cleaved with HF in the presence of anisole.

EXAMPLE 4

L-Tyrosyl-D-C-phenylglycyl-glycyl-L-phenylalanyl-D-arginyl amide

Following the procedures set forth in examples 1 and 2, with the exception that Boc-D-Arg(Tos)-OH is initially introduced into the benzhydrylamine resin rather that Boc-D-Lyz(Clz)-OH, yields the title compound.

EXAMPLE 5

L-Tyrosyl-D-C-phenylglycyl-glycyl-L-phenylalanyl-D-leucyl amide

Repetition of the procedure of examples 1 and 2, employing Boc-D-Leu-OH rather than Boc-D-Lys-(Clz)-OH as the initial amino acid introduced into the benzhydryl amine resin, affords the title compound.

EXAMPLE 6

L-Arginyl-L-tyrosyl-D-C-phenylglycyl-glycyl-L-phenylalanyl-D-leucyl amide

The peptido resin of example 1 is treated in the solid phase reactor with four equivalents of Boc-L-Arg(Tos)-OH in accordance with schedule A. The resulting peptido resin is cleaved with HF in the presence of anisole and purified in the manner detailed in example 2 to obtain the title compound.

EXAMPLE 7

L-Ornithyl-L-tyrosyl-D-C-phenylglycyl-glycyl-L-phenylalanyl-D-leucyl amide

The peptido resin of example 1 is treated in the solid phase reactor with four equivalents of Boc-L-Orn(Clz)-

OH in accordance with schedule A. The resulting peptido resin is cleaved with HF in the presence of anisole and the polypeptide is worked up following the procedure detailed in example 2 to afford the title compound.

EXAMPLE 8

L-Tyrosyl-D-C-phenylglycyl-glycyl-L-phenylalanyl-D-lysyl-OH

Chloromethylated polystyrene resin is esterified with Boc-D-Lys(Clz)-OH according to the procedure of Gisin, *Helv. Chim. Acta.,* 56,1976 (1973) and the polymeric ester is treated according to schedule A of example 1 for icorporation of Boc-Phe-OH, Boc-Gly-OH, Boc-D-Pgl-OH and Boc-Tyr(Bzl)-OH. The resulting peptido resin is treated according to the procedure of example 2 to yield the title pentapeptidic acid.

EXAMPLE 9

L-Tyrosyl-D-C-phenylglycyl-glycyl-L-phenylalanyl-D-lysyl ethylamide

Treatment of the peptido resin of example 8 with ethylamine in a sealed flask for 10 hours followed by removal of excess ethylamine, extraction with DMF filtration and evaporation of the filtrate yields the title ethylamide.

EXAMPLE 10

L-Lysyl-N-methyl-L-tyrosyl-D-phenylglycyl-glycyl-L-phenylalanyl-D-lysyl amide

The procedure of example 1 is repeated, with the exception that the last amino acid introduced into the solid phase reactor is Boc-N-methyl-L-tyrosyl(Bzl)-OH. That coupling is followed by the introduction of Boc-L-Lys(Clz)-OH. The peptido resin is cleaved and worked up in accordance with the procedure of example 2 to yield the title compound.

What is claimed is:

1. A polypeptide of the formula:

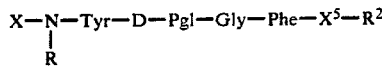

in which
X is hyrdogen, Arg, Lys or Orn;
$X^5$ is D-Lys, D-Arg, D-Met or D-Leu;
R is hydrogen, methyl, allyl or cyclopropylmethyl; and
$R^2$ is —OH, $NH_2$ or —$NHC_nH_{2n+1}$, where n is 1,2,3 or 4 providing that when X is hyrogen then $X^5$ cannot be D-Met or D-Leu; or a pharmaceutically exceptable salt thereof.

2. The compound of claim 1 which is Tyr-D-Pgl-Gly-Phe-D-Lys-$NH_2$ or a pharmaceutically acceptable salt thereof.

3. The compound of claim 1 which is Tyr-D-Pgl-Gly-Phe-D-Arg-$NH_2$ or a pharmaceutically acceptable salt thereof.

4. The compound of claim 1 which is Arg-Tyr-D-Pgl-Gly-Phe-D-Leu-$NH_2$ or a pharmaceutically acceptable salt thereof.

5. The compound of claim 1 which is Orn-Tyr-D-Pgl-Gly-Phe-D-Leu-$NH_2$ or a pharmaceutically acceptable salt thereof.

6. The compound of claim 1 which is Tyr-D-Pgl-Gly-Phe-D-Lys-OH or a pharmaceutically acceptable salt thereof.

7. The compound of claim 1 which is Tyr-D-Pgl-Gly-Phe-D-Lys-$NHC_2H_5$ or a pharmaceutically acceptable salt thereof.

8. The compound of claim 1 which is Lys-N-methyl-Tyr-D-Pgl-Gly-Phe-D-Lys-$NH_2$ or a pharmaceutically acceptable salt thereof.